US008016264B2

(12) United States Patent
Takemasa et al.

(10) Patent No.: US 8,016,264 B2
(45) Date of Patent: Sep. 13, 2011

(54) ROTARY-VALVE AND ADSORPTION SEPARATION SYSTEM

(75) Inventors: Kenji Takemasa, Yamaguchi (JP); Toshihiko Fuse, Hyogo (JP); Mitsuru Kudari, Hyogo (JP); Masanobu Ninomiya, Hyogo (JP)

(73) Assignees: Teijin Pharma Limited, Tokyo (JP); Nippon Pillar Packing Co., Ltd., Osaka (JP)

( * ) Notice: Subject to any disclaimer, the term of this patent is extended or adjusted under 35 U.S.C. 154(b) by 281 days.

(21) Appl. No.: 12/226,349

(22) PCT Filed: Apr. 26, 2007

(86) PCT No.: PCT/JP2007/059437
§ 371 (c)(1),
(2), (4) Date: Oct. 16, 2008

(87) PCT Pub. No.: WO2007/129679
PCT Pub. Date: Nov. 15, 2007

(65) Prior Publication Data
US 2009/0071341 A1 Mar. 19, 2009

(30) Foreign Application Priority Data
May 2, 2006 (JP) .................. 2006-128180

(51) Int. Cl.
*F16K 11/074* (2006.01)
*F16K 3/08* (2006.01)
*A61M 16/10* (2006.01)
*B01D 53/047* (2006.01)

(52) U.S. Cl. ..... 251/208; 251/314; 251/368; 128/205.24
(58) Field of Classification Search ................ 96/116, 96/121, 124; 95/130; 128/205.12, 205.24; 251/180, 314, 368, 208
See application file for complete search history.

(56) References Cited

U.S. PATENT DOCUMENTS
6,063,161 A * 5/2000 Keefer et al. ............ 95/100
6,664,572 B2 * 12/2003 Chatufale ............... 257/172

FOREIGN PATENT DOCUMENTS
| JP | 63-36765 U | 3/1988 |
| JP | 05-60254 A | 3/1993 |
| JP | 06-22670 U | 3/1994 |
| JP | 06-59670 U | 8/1994 |

(Continued)

OTHER PUBLICATIONS
Machine generated English translation of JP 2001-349630 A, published Dec. 2001.*

(Continued)

*Primary Examiner* — Frank M Lawrence
(74) *Attorney, Agent, or Firm* — Rader, Fishman & Grauer PLLC (57) ABSTRACT

A rotary valve comprising sliding members for supplying treatment gas containing water vapor to a plurality of treatment processes is provided. The rotary valve comprises sliding members (1, 2; 4, 6), through which open flow passages (8, 9, 10), having sliding surfaces slidable to each other and a mechanical seal mechanism for switching the flow passages (8, 9, 10) while sealing fluid by preliminarily pressing the sliding surfaces, wherein the sliding surface of each sliding members (1, 2; 4, 6) is made of hydrophobic material (2, 4) different in hardness from the other.

6 Claims, 5 Drawing Sheets

FOREIGN PATENT DOCUMENTS

| | | |
|---|---|---|
| JP | 07-508205 A | 9/1995 |
| JP | 2001-349630 A | 12/2001 |
| JP | 2004-209263 A | 7/2004 |
| JP | 2005-109215 A | 4/2005 |
| WO | WO-93/16786 A1 | 9/1993 |
| WO | WO-02/053446 A1 | 7/2002 |

OTHER PUBLICATIONS

TUFRAM brocure, General Magnaplate Corp, 2006.*
International Search Report mailed on Jun. 12, 2007.

* cited by examiner

ROTARY-VALVE AND ADSORPTION SEPARATION SYSTEM

TECHNICAL FIELD

The present invention relates to a rotary valve for switching a fluid passage by the mutual sliding rotary motion between a rotary member and a stationary member, and particularly to a rotary valve for switching a flow passage of a pressure swing adsorption (SPA) type oxygen concentrator for separating oxygen in air and supplying the same to a respiratory patient or others. The present invention also relates to an adsorption separation system using such a rotary valve.

BACKGROUND ART

Recently, there is the tendency in that patients suffered from respiratory diseases such as pulmonary emphysema or chronic bronchitis have increased. One of most effective treatments for such diseases is an oxygen inhalation therapy. On the other hand, an oxygen condenser for separating oxygen-condensed gas directly from air has been developed and gradually prevailed as a treatment device for the oxygen-inhalation therapy due to the convenience when used and the easiness of maintenance.

As such an oxygen condenser, an absorption type filled with absorbent capable of selectively adsorbing nitrogen has been known. Of them, a pressure swing adsorption (SPA) type oxygen concentrator using an air compressor as means for supplying air has been used as a device for the at-home oxygen inhalation therapy. This device generally repeats, at a constant cycle, and an adsorption process for obtaining oxygen-condensed gas by supplying compressed air from a compressor to one or more adsorption beds filled with absorbent capable of selectively adsorbing nitrogen so that nitrogen is adsorbed under a pressed condition, a desorption process for desorbing the nitrogen by decreasing an inner pressure of the adsorption beds to regenerate the absorbent. If necessary, for the purpose of improving the absorbent-regeneration efficiency and rising the pressure, directly before finishing the desorption process, a pressure-equalizing process may be added wherein part of the obtained dry oxygen-condensed gas is made to reversely flow. Thus, the oxygen-condensed gas is obtained. Generally, by connecting the compressor to the fluidized bed by piping via valve means, a flow passage control for switching a pressurized air passage to the fluidized bed is carried out. Such a flow passage switching apparatus is, however, problematic in that the number of parts increases and the maintenance becomes troublesome.

To improve such inconveniences, modulated oxygen condensers are proposed wherein pressurized air is supplied to the adsorption bed via a fluid separation device having a rotary valve therein described in Japanese Unexamined Patent Publication (Kohyo) No. H7-508205 (Patent Document No. 1) and Japanese Unexamined Patent Publication (Kokai) No. 2004-209263 (Patent Document No. 2). Such oxygen condensers must be small in size when used for an at-home therapy, and thus, it is difficult to provide a sufficient space for the mechanically sealed rotary and stationary valve sections within the valve. Instead, a mechanical seal structure is adopted wherein surfaces of a rotor which is a sliding member provided on a rotary shaft side to be rotatable with the rotary shaft and a stator provided on a non-rotatable housing side, which surfaces are perpendicular to a rotary axis, are in tight contact with each other while loaded in the axial direction by pressing means such as a spring to prevent fluid from leaking out of the periphery of the shaft.

In the conventional mechanical seal, lubricant such as oil is used for decreasing the sliding resistance between the sliding surfaces. In a valve used in the oxygen condenser for switching flow passages of breathing gas, however, such lubricant could not be used. Accordingly, it has been designed so that the flatness of the sliding surfaces is extremely improved to lower the sliding resistance.

DISCLOSURE OF THE INVENTION

The inventors of the present invention have found that when gas having the condensation property such as pressurized air containing moisture is connected to such a valve, liquid such as water is condensed due to the liquidized condensation phenomenon in the flow passage or the capillary condensation on the sliding surface of the valve, and if a small amount of liquid enters between the sliding surfaces, a surface tension temporarily becomes dominant to extremely rise the sliding resistance, resulting in the increase in rotary torque. While there are no problems if a motor having a rotary torque larger than such the increase in torque is used, in a system using a motor rotatable by a minimum torque for the purpose of minimizing a size and/or a weight of the system, there might be a problem in a high humidity environment in that the rotary speed is lowered or zero.

An object of the present invention is to provide a rotary valve as means for solving the above-mentioned problem or an adsorption separation system mounting such a rotary valve.

The inventive rotary valve comprises two sliding members, through which open flow passages, having sliding surfaces slidable to each other and a mechanical seal mechanism for switching said flow passages while sealing fluid by preliminarily pressing said sliding surfaces, wherein said sliding surface of each said sliding members is made of hydrophobic material and the other surface opposite to said sliding surface is made of material higher in rigidity than said hydrophobic material; said hydrophobic material and said higher rigidity material being bonded together to be one-piece.

Also, the inventive rotary valve comprises two sliding members, through which open flow passages, having sliding surfaces slidable to each other and a mechanical seal mechanism for switching said flow passages while sealing fluid by preliminarily pressing said sliding surfaces, wherein each said two sliding members has hydrophobic nature and is different in rigidity from the other on at least said sliding surface side.

Also, the inventive adsorption separation system of a pressure swing adsorption (SPA) type comprises a plurality of adsorption beds filled with absorbent, means for supplying treatment gas to said adsorption beds and a flow passage switching member for subsequently pressurizing and supplying treatment gas from said supplying means to said adsorption beds and adsorbing and desorbing the treatment gas at a constant timing, wherein said flow passage switching member is a rotary valve comprising two sliding members, each having a sliding surface slidable to the other; a gas supplying port for supplying treatment gas and a gas exit for discharging the gas after the treatment being provided on said slidable surface of one sliding member, and a distribution groove being formed on said sliding surface of the other sliding member; said switching surfaces being slid to each other while sealed by a mechanical seal wherein each said two sliding members has hydrophobic nature at least on said sliding surface side thereof and is different in rigidity from the other.

BEST MODE FOR CARRYING OUT THE INVENTION

Embodiments of the present invention will be described in detail below with reference to the attached drawings.

A rotary valve according to the present invention consists of a stator (stationary member) having a plurality of ports connected to fluid-flowing passages on a surface thereof and a rotor (rotary member) having a connection passage on a surface thereof for switching the mutual connection of the ports by the rotary motion of the rotor, wherein the surface of the stator having the ports (flow passages) and that of the rotor having the connection passage are rotationally slid to each other to switch the connection of the fluid-flowing passages. The connection passage of the rotor may be of various shapes in accordance with the number or the arrangement of the ports on the stator. The rotary valve according to the present invention is characterized in that at least part of the sliding members; i.e., the stator and the rotor; including the sliding surfaces thereof are made of hydrophobic material. When gas having the condensation property such as pressurized air containing moisture comes into contact with such a valve, liquid such as water is condensed due to the liquidized condensation phenomenon in the flow passage or the capillary condensation on the sliding surface of the valve, and if a small amount of liquid enters between the sliding surfaces, a surface tension temporarily becomes dominant. According to the present invention, by using the rotary valve having the sliding surface made of hydrophobic material, it is possible to prevent such phenomena from occurring, whereby the abnormal rise of the sliding resistance or the rotary torque is avoidable.

The rotary valve of this type is particularly effective when the flow passage for gas having the condensation property such as air containing water is switched. In such a case, the exit ports are provided preferably around the flow passage for the gas having the condensation property, and particularly in the valve for switching air containing water vapor, the air is guided from a central entrance port to the exit ports around the pressurized air flow passages via the connection flow passages so that the rise of the torque is avoidable even if the moisture condensation occurs.

In the rotary valve, a single connection flow passage is provided on the surface of the rotor when the number of ports is few. Contrary to this, when the number of ports is much, a plurality of openings are provided on the same radius of the sliding surface of the rotor, and connected to each other on the back of the sliding surface by a flow passage.

The hydrophobic material used for the sliding members; i.e., the stator and rotor; may be of a fluorine type or a silicon type, such as polytetrafluoroethylene resin (PTFE), polyether-etherketon resin (PEEK) or polyacetal resin (POM). Particularly, the fluorine type hydrophobic resin is preferably cited. Further, such material may be improved in slidability and/or strength by adding filler thereto, for example, PTFE resin added with polyimide fibers as filler or that added with carbon or polyethylene fibers. As an index indicating the hydrophobic property of these materials, a water drop contact angle is generally used, wherein 90° or more is preferable. The material satisfying this condition is the above-mentioned PTFE resin.

If the sliding surfaces of the two sliding members are made of the same material, there is a phenomenon in that both the sliding surfaces are worn together since the both have the same hardness. Also, an abnormal wear such as the condensation wear may occur since the same material is used for both the surfaces. To solve such defects, it is adapted that the hardness of one surface is lower than that of the other to positively wear the softer one which is then exchanged to a fresh one. If PTFE resin added with polyimide having a somewhat higher hardness is used for forming the stator side, while PTFE resin added with carbon having a lower hardness is used for forming the rotor side, it is possible to prepare the rotor as a member to be exchanged.

While the sliding surfaces are made of hydrophobic resinous material as described above, the resinous material is less in mechanical strength even if additives are added thereto, and the deformation may occur when they are sealed by using the pressure of a spring as a mechanical seal. Accordingly, part of a structural body to be loaded is made of high-rigidity material such as metal including SUS, aluminum or brass, ceramics or composite material.

The hydrophobic material and the material higher in rigidity than the former may be bonded together by the surface modification, coating, impregnation or adhesion. The surface modification is generally carried out by adhering self-systemized monomolecular film, DLC film, preferably that added with fluorine to a substrate. The coating is generally a PTFE coating. The impregnation is generally carried out by impregnating the hydrophobic material into voids or slits on the substrate surface.

The adhesion is generally carried out by adhering PTFE resin or PTFE type resin to metal, preferably stainless steel, resulting in a sliding member. Generally, since the PTFE resin or PTFE type resin is not good in adhesiveness, the surface to be adhered may be treated with alkaline etching to remove the fluorine group from the surface so that the wettability thereof to the epoxy type adhesive or others is ensured. Further, for the purpose of increasing the area to be adhered, the surface may be air-blasted.

The inventive rotary valve is applicable to the pressure swing adsorption type oxygen concentration system. That is, the pressure swing adsorption type oxygen concentration system includes adsorption beds filled with absorbent capable of selectively absorbing nitrogen rather than oxygen, air supplying means for supplying pressurized air to the adsorption beds, and oxygen supplying means for supplying oxygen-condensed air generated from the adsorption beds to the user. This system has the above-mentioned inventive rotary valve as a flow passage switching valve in a flow passage for supplying the pressurized air from air supplying means such as a compressor to the adsorption beds.

EXAMPLES

Figure 1:
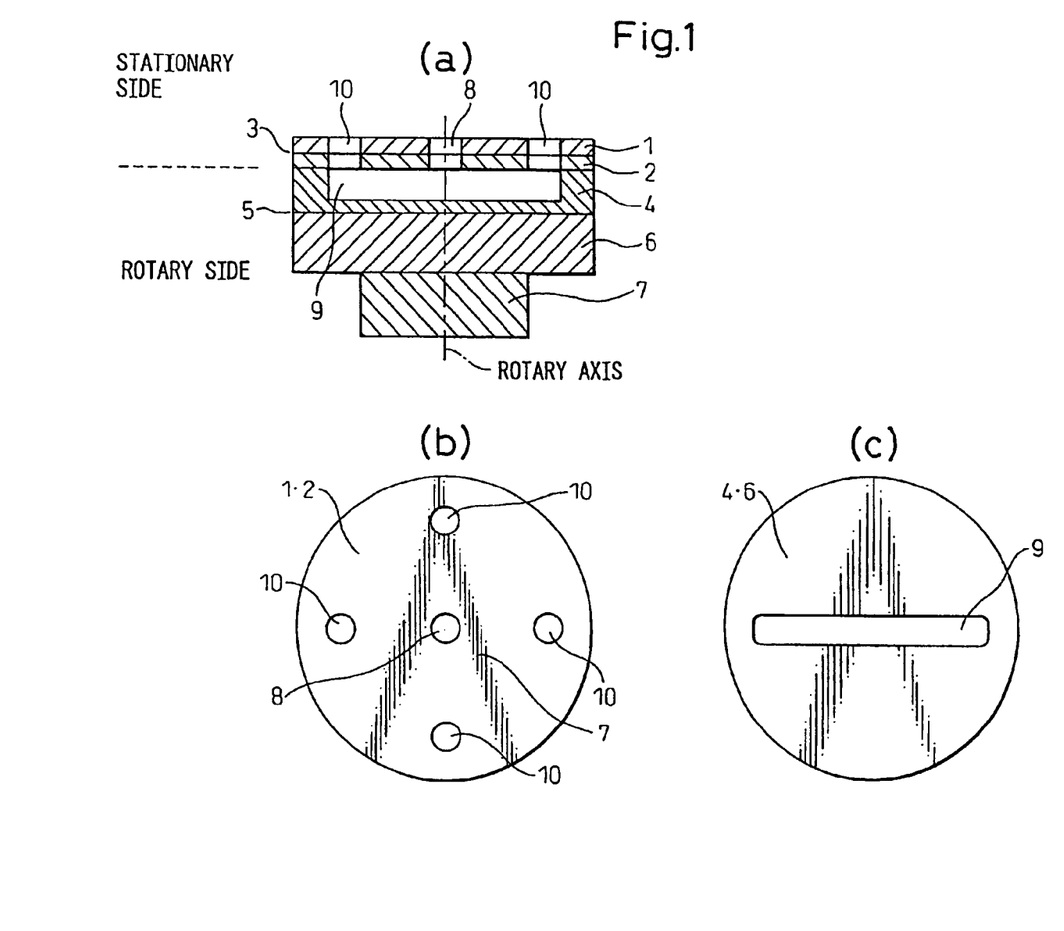
FIG. 1 illustrates a structure of Embodiment 1 of a slidable valve according to the present invention wherein part of a surface layer thereof including the sliding surface is made of hydrophobic material.
Figure 2:
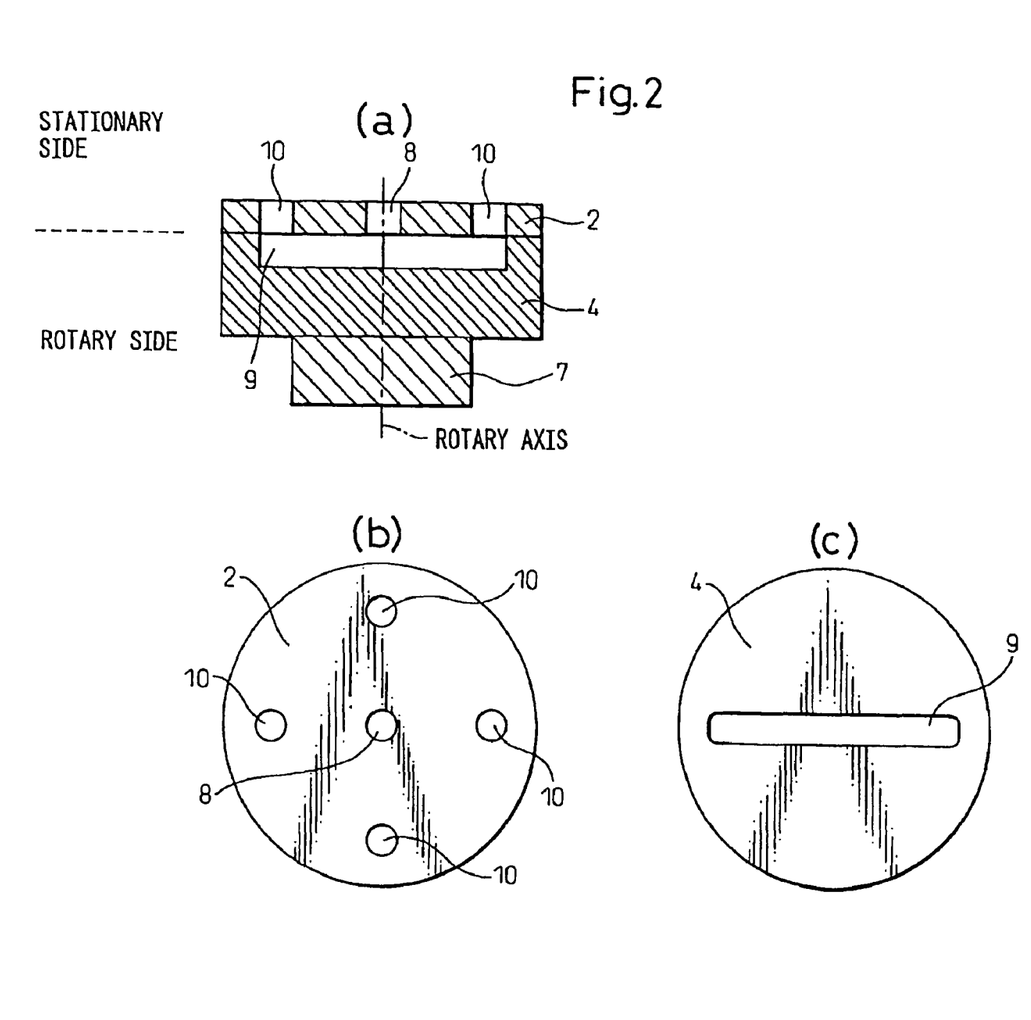
FIG. 2 illustrates a structure of Embodiment 2 of a slidable valve according to the present invention wherein all of a surface layer thereof including the sliding surface is made of hydrophobic material.
Figure 3:
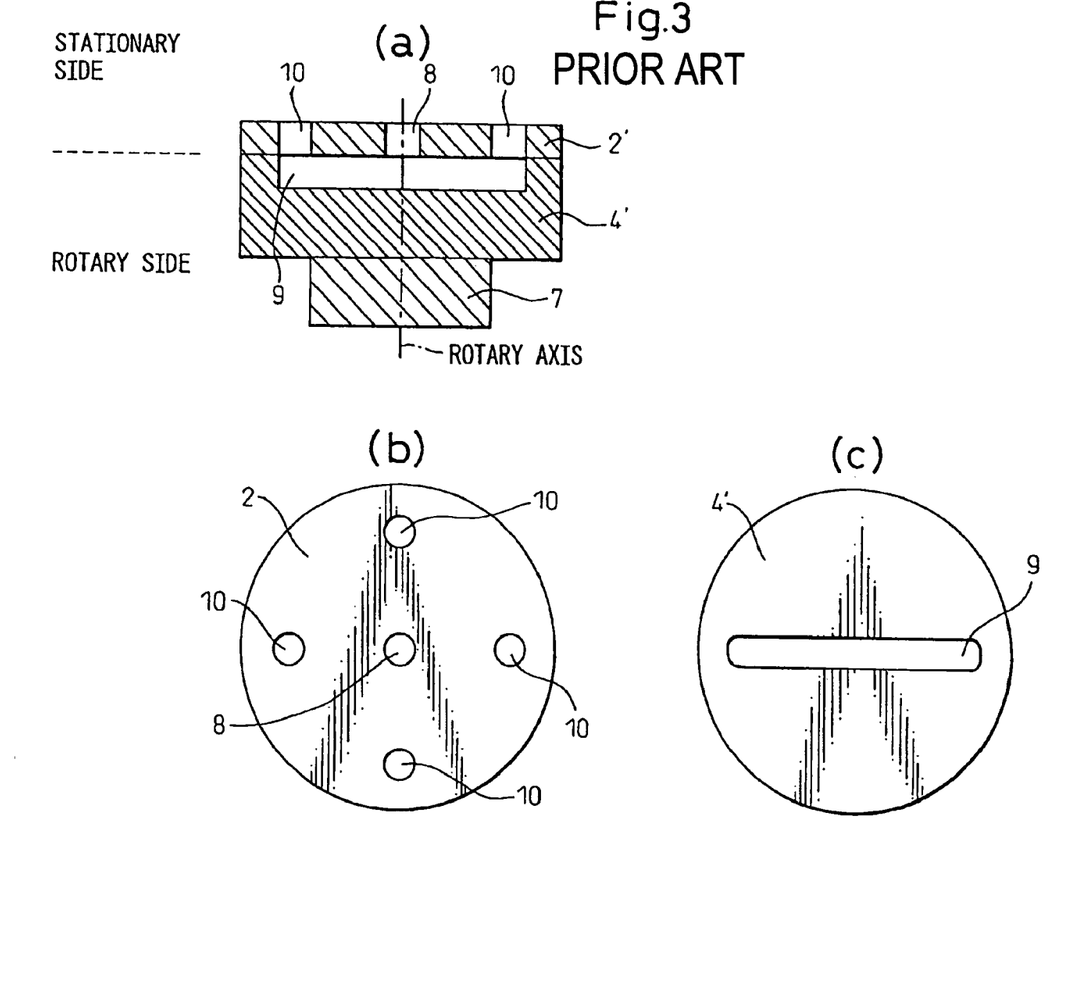
FIG. 3 illustrates a structure of a prior art slidable valve.

Some preferable embodiments of the rotary valve of the present invention will be described below with reference to the drawings, wherein FIG. 1 illustrates Example 1 of the inventive rotary valve; FIG. 2 illustrates Example 2 thereof; and FIG. 3 illustrates a prior art rotary valve as a comparative example.

Example 1

Example 1 of the inventive rotary valve will be described in accordance with the structure shown in FIG. 1. The rotary valve of Example 1 is a slidable valve for supplying air containing water vapor taken from atmosphere to a plurality of treatment processes, part of which outer layer including the sliding surfaces is made of hydrophobic material.

Rotary members 4, 6 and 7 are perpendicularly pushed onto stationary members 1, 2 by a reactive force of a spring not shown. The rotary members 4, 6 are bonded together via a bonding surface 5 to be one-piece. Similarly, the stationary members 1, 2 are bonded together via a bonding surface 3 to be one-piece.

One member 4 of the rotary members 4, 6 disposed on the sliding surface side is made of PTFE type resin. This PTFE type resin is PTFE resin added with carbon as filler, (which is H4C grade, manufactured by NIPPON PILLAR PACKING CO., LTD.) The other member 6 of the rotary members 4, 6 disposed opposite to the sliding surface is made of SUS-304. The bonding of the rotary members 4, 6 is carried out by adhering the alkaline-etched surface of the PTFE type resin of the member 4 to the SUS-304 surface of the member 6.

One member 2 of the stationary members 1, 2 disposed on the sliding surface side as a hydrophobic material is made of PTFE type resin. This PTFE type resin is PTFE resin added with polyimide as filler, which is, Y2A grade, manufactured by NIPPON PILLAR PACKING CO., LTD.

The other member 1 of the stationary members 1, 2 disposed opposite to the sliding surface is made of SUS-304, which material is higher in rigidity than the member 2 made of hydrophobic material. The bonding of the stationary members 1, 2 is carried out by adhering the alkaline-etched surface of the PTFE type resin constituting the hydrophobic member 2 to the SUS-304 surface of the member 1.

The spring, not shown, but described above provides a sealing pressure to preventing air from leaking out of the sliding surface. A motor driving device (power source), also not shown, generates a driving torque which is transmitted via a rotary shaft 7 to rotate the rotary members 4, 6 at a constant speed (for example, 2 to 5 rpm). The air containing water vapor is compressed by a compressor, not shown, and supplied from gas supplying openings (ports) 8 provided on the sealing surface of the stationary members 1, 2 (FIG. 1(*b*)). The treatment gas is supplied from four gas exits (ports) 10 provided in the stationary members 1, 2 to four treatment processes via a distribution groove (connection flow passage) 9 provided on a seal surface (FIG. 1(*c*)) in the rotary members 4, 6 at a timing at which positions of the ports 10 coincide with that of the distribution groove 9.

The rotary valve according to Example 1 is capable of carrying out a continuous operation for a long period in a stable state even if the condensation of water occurs in an environment wherein the temperature and humidity of air containing water vapor taken from the atmosphere as well as the temperatures of the stationary members 1, 2 and the rotary members 4, 6 vary, because a rise of torque thereby is slight and no leakage occurs from the sliding surface.

Example 2

Next, Example 2 of the inventive rotary valve will be described in accordance with FIG. 2. In the rotary valve of Example 2, all of a surface layer section including the sliding surface for supplying air containing water vapor, taken from the atmosphere, to a plurality of treatment processes is made of hydrophobic material.

The stationary member 2 is made of a single material of PTFE type resin; in this Example, Y2A grade manufactured by NIPPON PILLAR PACKING CO., LTD. Also, the rotary member 4 is made of a single material of PTFE type resin; in this Example, H4C manufactured by NIPPON PILLAR PACKING CO., LTD. Other structures are the same as Example 1.

In the same manner as Example 1, the rotary valve of Example 2 is capable of carrying out a continuous operation for a long period in a stable state even if the condensation of water or occurs in an environment wherein the temperature and humidity of air containing water vapor taken from the atmosphere as well as the temperatures of the stationary members 1, 2 and the rotary members 4, 6 vary, because a rise of torque thereby is slight and no leakage occurs from the sliding surface.

Comparative Example

Next, a rotary valve which has been conventionally used in the prior art using sliding members made of hydrophilic material will be described in accordance with FIG. 3 as a Comparative Example 1 of the rotary valve of the present invention. A ceramic material is used as a stationary member 2'. A carbon material (carbon or graphite) which is commonly used as solid lubricant as a rotary member 4'.

According to the rotary valve of the Comparative Example 1, the torque rises over the maximum torque of the motor driving device due to condensation and the rotation defect occurs, when it is operated under the conditions that the condensation of water occurs in an environment wherein the temperature and humidity of air containing water vapor taken from the atmosphere as well as the temperatures of the stationary member 2' and the rotary member of solid lubricants 4' vary.

Modified Examples

While Examples of the present invention were described above with reference to the attached drawings, the present invention should not be limited to the above-mentioned Examples 1 and 2, but includes various changes, modifications or alternations within a spirit or scope of the present invention. For example, in the respective Examples of the rotary valve described above, the rotary valve may be used for distributing treatment gas to a system including a plurality of adsorption tubes, reactors or dust collectors.

Also, by combining sliding members used in Examples 1 and 2 to be a one-piece structure as Example 1, the stationary member may consist of a hydrophobic member 2 on the sliding surface side and a high-rigidity member 1 bonded to the former opposite to the sliding surface side to be a one-piece structure as in Example 1, while the rotary member may be a single hydrophobic member 4 as in Example 2. Contrary to this, the stationary member may be a single hydrophobic member 2 as in Example 1, while the rotary member may be a one-piece structure as in Example 1 wherein the hydrophobic member 4 on the sliding surface side and the high-rigidity member 6 opposite to the sliding surface are bonded together.
(Verification of Effects)

Figure 4:
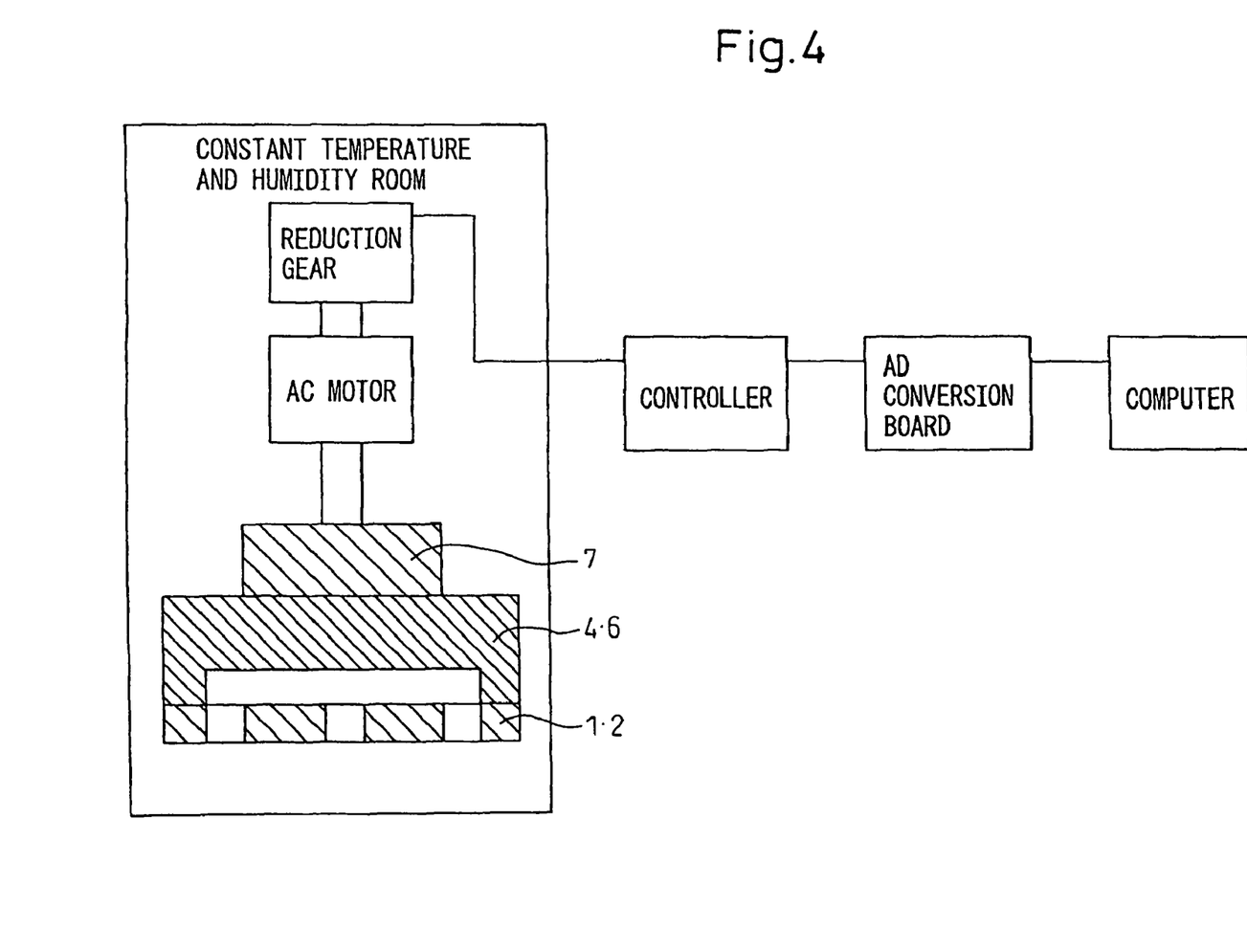
FIG. 4 is a block diagram of a device for testing the moisture-dependence of the sliding torque.

By using the rotary valves in Examples 1 and 2 and Comparative Example 1, the influence of surface tension of water condensed on the sliding surface was quantitatively evaluated. Concretely, the test was conducted by measuring the sliding torque while changing the atmospheric humidity around the sliding members to generate condensed water between the sliding surfaces in a high-humidity environment. FIG. 4 illustrates the block diagram of the torque measuring device. The change of the sliding torque in the high-humidity environment was observed in a constant temperature and humidity room while maintaining the temperature at a constant value and changing the relative humidity stepwise.

Figure 5:
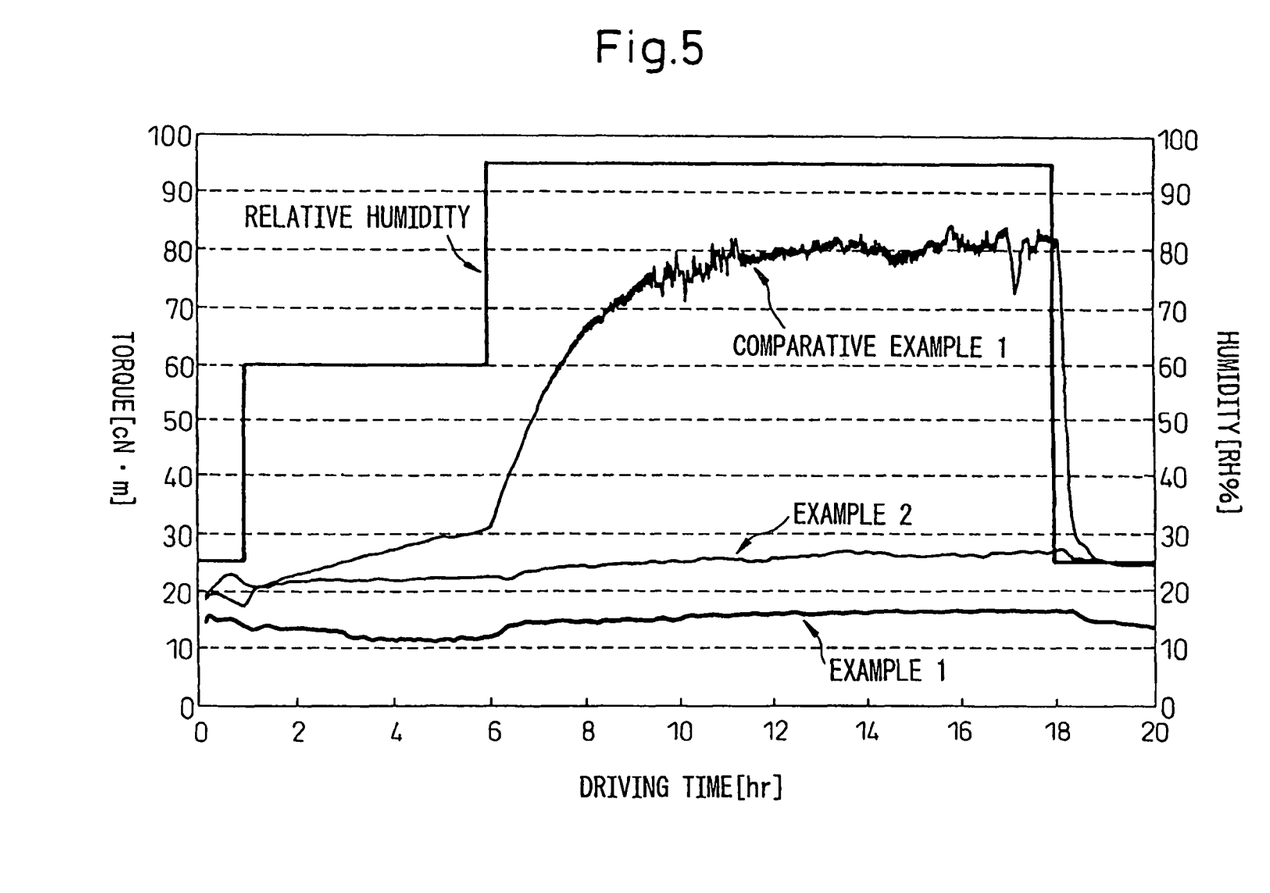
FIG. 5 illustrates a test result of the moisture-dependence of the sliding torque.

The test results are shown in FIG. 5. In Examples 1 and 2, the rise of torque due to the surface tension of the condensed water generated between the sliding surfaces is improved to a large extent in comparison with Comparative Example 1.

CAPABILITY OF EXPLOITATION IN INDUSTRY

According to the rotary valve of the present invention and the adsorption separation system mounting such a valve, it is possible to minimize the fluctuation of the sliding resistance of the rotary valve against the change in the driving environment between the low and high humidity atmospheres. Accordingly, the stable driving of the adsorption separation system using the inventive rotary valve, such as the pressure swing adsorption (PSA) type oxygen concentrator.

The invention claimed is:

1. A rotary valve comprising:
    two sliding members, through which open flow passages, having sliding surfaces slidable to each other and a mechanical seal mechanism for switching said flow passages while sealing fluid by preliminarily pressing said sliding surfaces,
    wherein said sliding surface of each said sliding members is made of hydrophobic material and the other surface opposite to said sliding surface is made of material higher in rigidity than said hydrophobic material;
    said hydrophobic material and said higher rigidity material being bonded together to be one-piece.

2. A rotary valve as defined by claim 1, wherein said hydrophobic material is polytetrafluoroethylene resin.

3. A rotary valve as defined by claim 1 or 2, wherein each of said two sliding members has hardness different from the other.

4. A rotary valve as defined by claim 3, wherein one of said sliding members is a stationary member and the other is a rotary member;
    said hydrophobic material of said rotary member being polytetrafluoroethylene resin added with carbon as filler, and said hydrophobic material of said stationary member being polytetrafluoroethylene resin added with polyimide as filler.

5. A rotary valve as defined by claim 1, wherein said higher rigidity material is metallic material.

6. A rotary valve comprising:
    two sliding members, through which open flow passages, having sliding surfaces slidable to each other and a mechanical seal mechanism for switching said flow passages while sealing fluid by preliminarily pressing said sliding surfaces,
    wherein each said two sliding members has hydrophobic nature and is different in rigidity from the other on at least said sliding surface side, wherein one of said sliding members is a stationary member and the other is a rotary member, and
    said hydrophobic material of said rotary member being polytetrafluoroethylene resin added with carbon as filler, and said hydrophobic material of said stationary member being polytetrafluoroethylene resin added with polyimide as filler.

* * * * *